(12) United States Patent
Hughes et al.

(10) Patent No.: US 8,183,866 B2
(45) Date of Patent: May 22, 2012

(54) **MAGNETIC RESONANCE TOMOGRAPHY METHOD AND APPARATUS WITH SEPARATION OF FAT AND WATER IMAGES ACCORDING TO THE TWO-POINT DIXON METHOD DEPENDENT ON $T_2^*$ DECAY**

(75) Inventors: Timothy Hughes, Erlangen (DE); Vladimir Jellus, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 276 days.

(21) Appl. No.: 12/617,904

(22) Filed: Nov. 13, 2009

(65) Prior Publication Data
US 2010/0123460 A1 May 20, 2010

(30) Foreign Application Priority Data
Nov. 14, 2008 (DE) .................. 10 2008 057 294

(51) Int. Cl.
*G01V 3/00* (2006.01)
(52) U.S. Cl. ..................... 324/309; 324/318
(58) Field of Classification Search .......... 324/300–322; 600/407–445
See application file for complete search history.

(56) References Cited

U.S. PATENT DOCUMENTS

| | | | | |
|---|---|---|---|---|
| 4,871,967 A | * | 10/1989 | Rotem et al. | 324/309 |
| 6,091,243 A | * | 7/2000 | Xiang et al. | 324/307 |
| 6,147,492 A | * | 11/2000 | Zhang et al. | 324/309 |
| 6,263,228 B1 | * | 7/2001 | Zhang et al. | 600/409 |
| 6,459,922 B1 | * | 10/2002 | Zhang | 600/410 |
| 2007/0247153 A1 | | 10/2007 | Yu et al. | |

OTHER PUBLICATIONS

"Separation of Water and Fat MR Images in a Single Scan at .35 T Using "Sandwich" Echoes," Zhang et al, Journal of Magnetic Resonance Imaging, vol. 6 (1969) pp. 909-917.
"Water-Fat Separation with Bipolar Multiecho Sequences," Lu et al, Magnetic Resonance in Medicine, vol. 60 (2008) pp. 198-209.
"Fast Spin-Echo Triple-Echo Dixon (fTED) Technique for Efficient $T_2$—Weighted Water and Fat Imaging," Ma et al, Magnetic Resonance in Medicine, vol. 58 (2007) pp. 103-109.
"Two-Point Water-Fat Imaging With Partially-Opposed-Phase (POP) Acquisition: An Asymmetric Dixon Method," Xiang, Magnetic Resonance in Medicine, vol. 56 (2006) pp. 572-584.

* cited by examiner

*Primary Examiner* — Brij Shrivastav
(74) *Attorney, Agent, or Firm* — Schiff Hardin LLP

(57) ABSTRACT

In a magnetic resonance tomography method and apparatus for separation of fat and water images according to the two-point Dixon method dependent on the $T_2^*$ decay, the following steps are implemented: (S1) acquire three fat-water images, respectively corresponding to the echo times TE1, TE2, TE3 after the RF excitation pulse, wherein first and third fat-water images exhibit the same phase, (S2) calculate a $T_2^*$ map from the two equiphase images, (S3) correct the $T_2^*$ influence in one of the two equiphase fat-water images and in the counter-phase fat-water image, and (S4) reconstruct a pure $T_2^*$-corrected fat image and a pure $T_2^*$-corrected water image according to the two-point Dixon method on the basis of the $T_2^*$-corrected equiphase and counter-phase fat-water images in Step (S3).

7 Claims, 8 Drawing Sheets

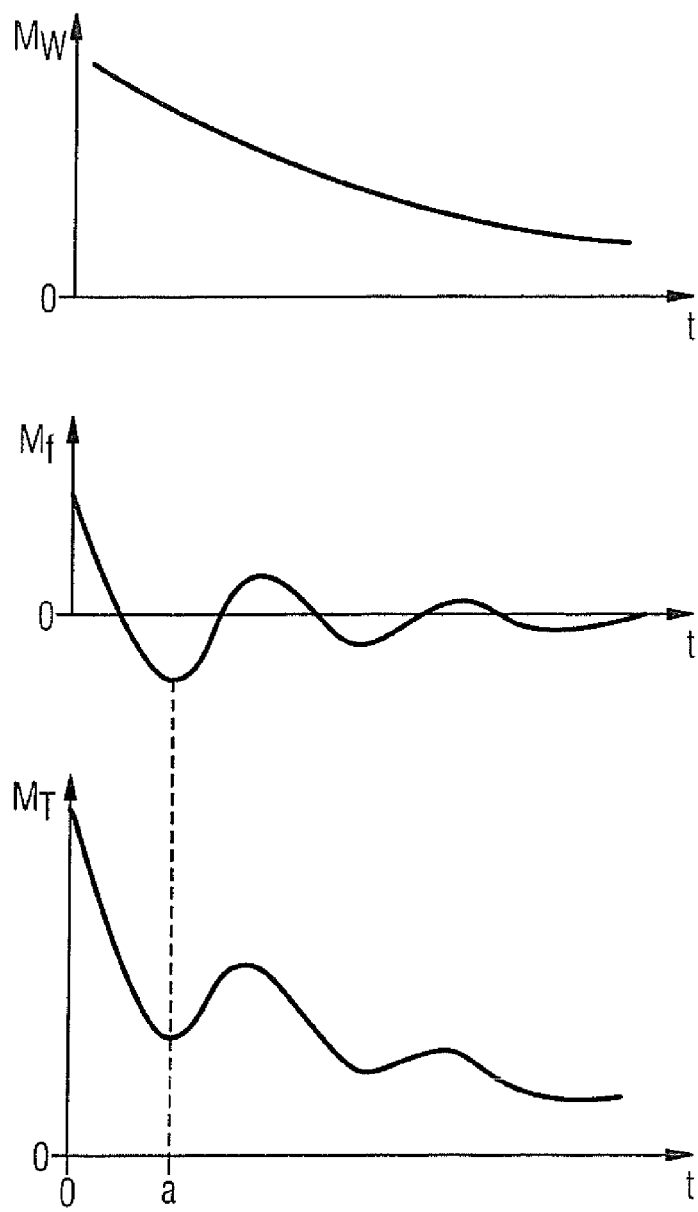

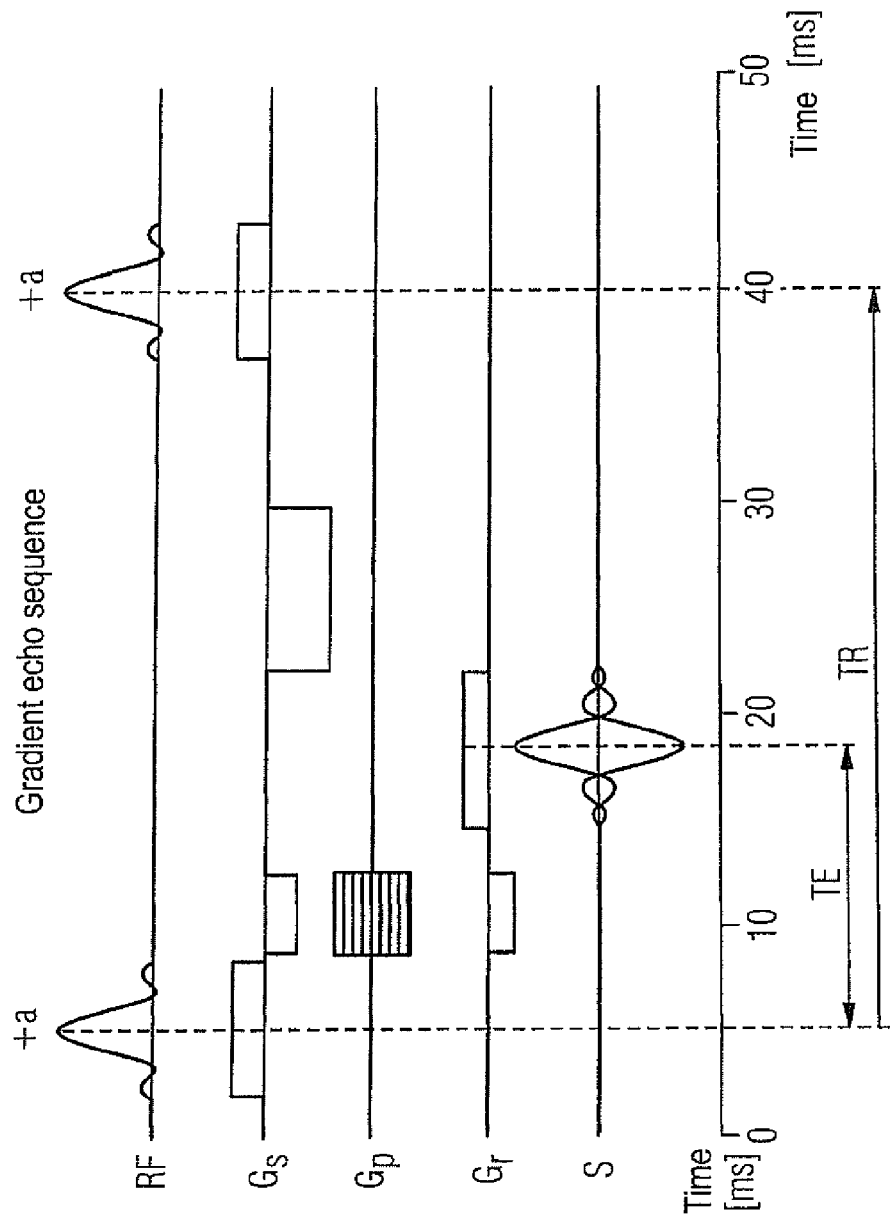

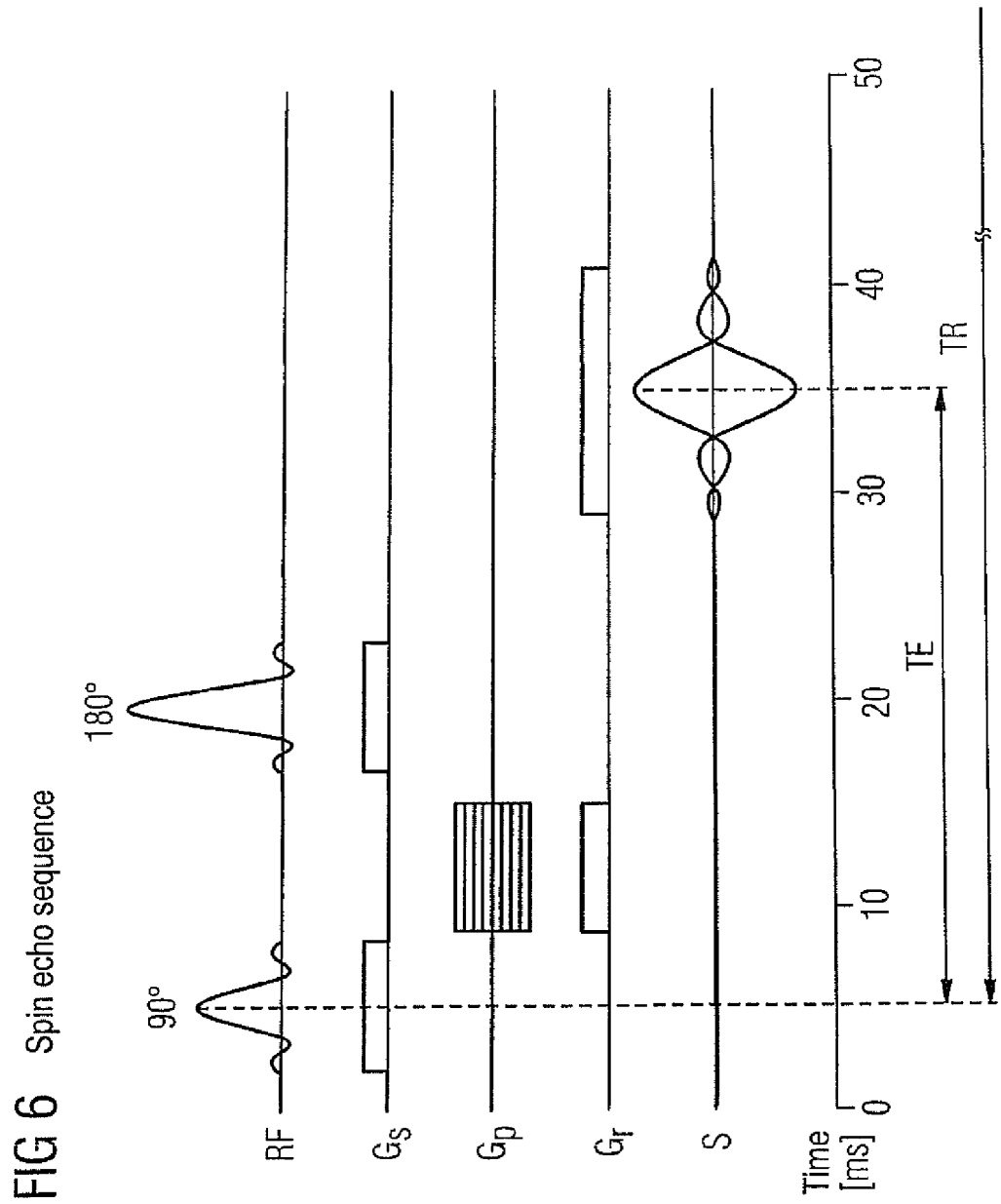

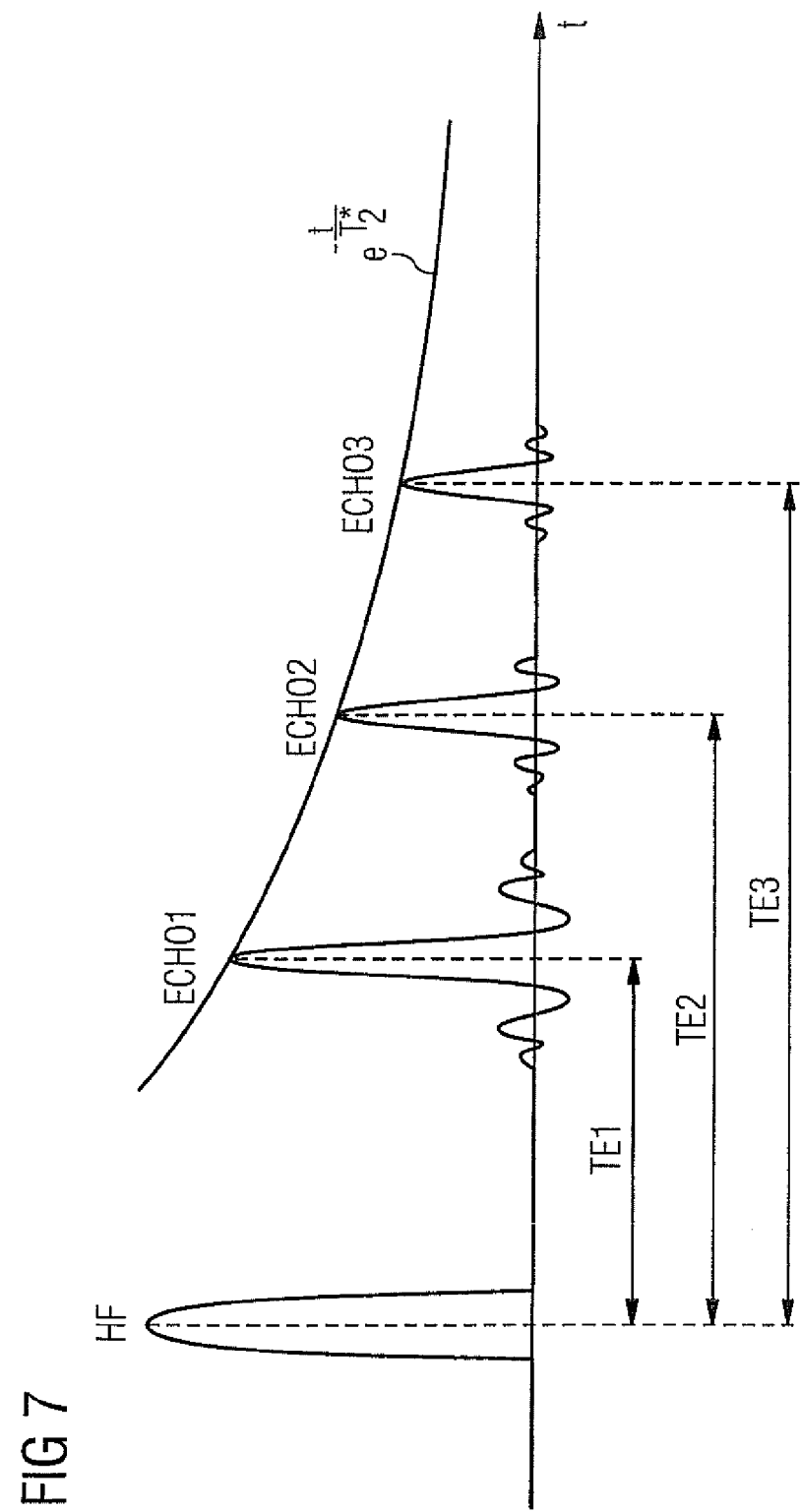

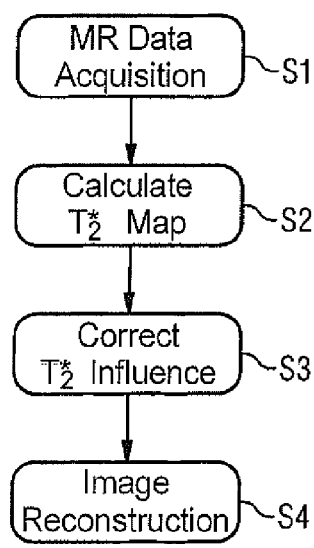

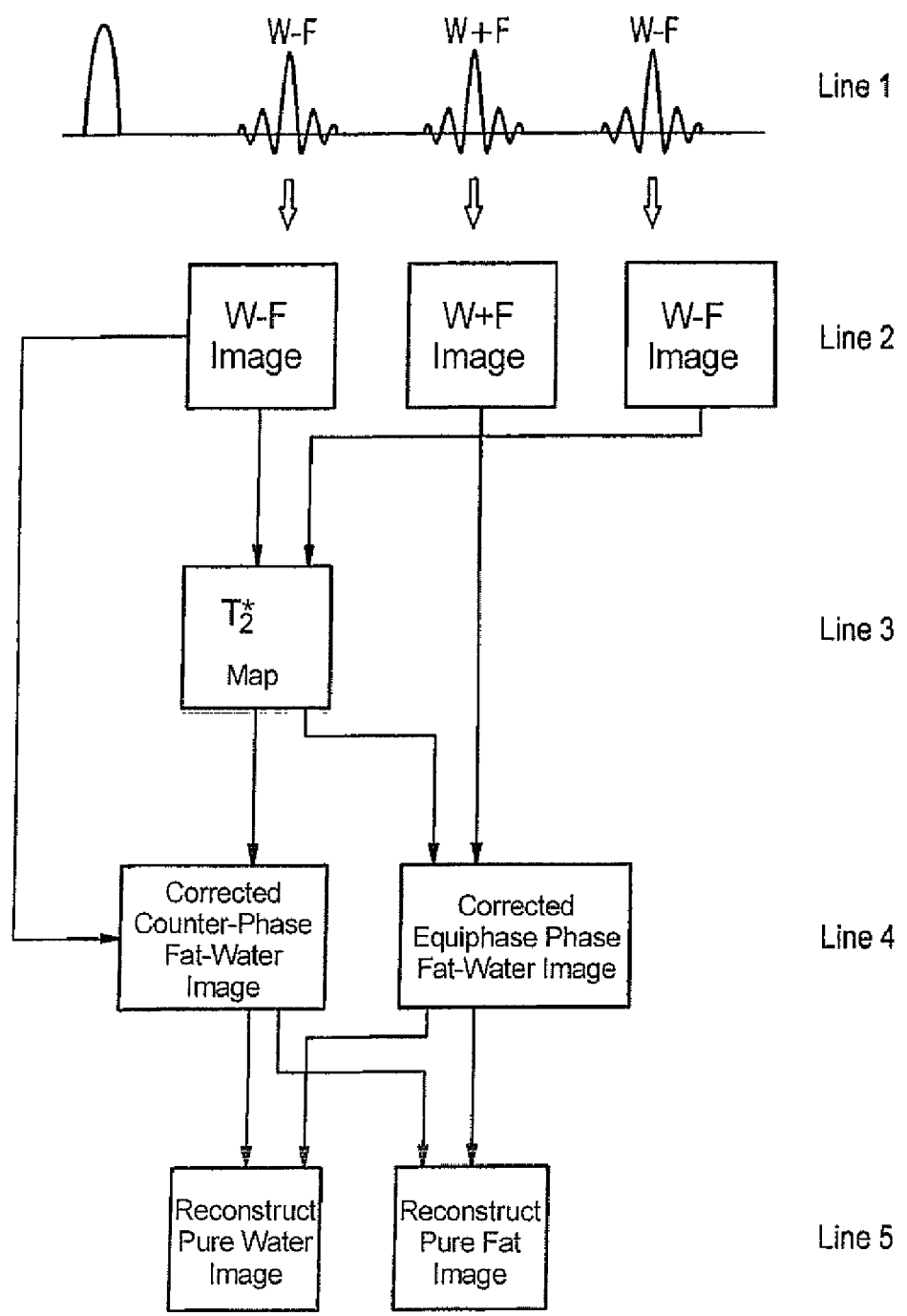

MAGNETIC RESONANCE TOMOGRAPHY METHOD AND APPARATUS WITH SEPARATION OF FAT AND WATER IMAGES ACCORDING TO THE TWO-POINT DIXON METHOD DEPENDENT ON $T_2^*$ DECAY

BACKGROUND OF THE INVENTION

1. Field of the Invention

The present invention generally concerns nuclear magnetic resonance tomography (MRT) in the field of medicine for examination of patients. The present invention in particular concerns a method and a magnetic resonance tomography apparatus to implement the method of the type making use of the two-point Dixon method.

2. Description of the Prior Art

Magnetic resonance tomography is a slice image method for medical diagnostics that is primarily characterized by a high contrast resolution capability. Due to the excellent ability to show the soft tissue, magnetic resonance tomography has developed into a method that is in many cases superior to x-ray computed tomography. Magnetic resonance tomography today is based on the application of spin echo and gradient echo sequences that enable an excellent image quality given measurement times on the order of minutes.

Obtaining fat images and water images of a patient represents a challenge in magnetic resonance imaging. Due to the influence of the chemical shift (see below), artifacts that must be corrected arise at the boundary layers between fat and water, but the fat signal represents valuable information (for example fat content in the liver) which should be maximized or optimized.

The property that the resonance frequency shifts slightly in proportion to the field strength depending on the type of chemical bond in which a signal-emitting nucleus participates, is known as chemical shift. Due to their concentration in the human body, hydrogen atoms in free water and in fat primarily contribute in the image. Their relative resonance frequency difference is approximately 3 ppm (parts per million). In the use of spin echo and gradient echo sequences, this leads to a modulation of the signal intensity depending on the echo time TE.

In the original publication by W. T. Dixon, a method was presented that achieves a separation of fat images and water images with two echoes (gradient or spin echoes). This is described briefly in the following.

The magnetization vector of the water protons $M_w$ and the magnetization vector of the fat protons $M_f$ point in the same direction immediately after radiation of a radio-frequency excitation pulse (typically with a flip angle of 90° in the case of a spin echo sequence, typically with much smaller flip angle given a gradient echo sequence). However, this state does not persist since the water protons in the homogeneous magnetic field precess 3 to 4 ppm more quickly than the fat protons. In a laboratory system (FIG. 2) it is seen how the magnetization of the water protons and that of the fat protons disperse with time. This difference amounts to approximately 50 Hz at 0.35 T. As shown in FIG. 3, the total magnetization $M_T$ is the vector sum of water magnetization and fat magnetization. FIG. 3 is based on a reference system that rotates with the frequency of the water protons.

FIG. 4 shows that the total magnetization $M_T$ initially (when the water magnetization and the fat magnetization point in the same direction) exhibits a maximum but soon traverses a minimum when the water magnetization and the fat magnetization are anti-parallel.

The first minimum occurs when $$t = \frac{1}{2(v_W - v_F)} = a$$

wherein t is thereby the time, $v_F$ is the fat proton frequency and $v_w$ is the water proton frequency. The time a is of great importance since the acquisition of an imaging sequence at time t=a delivers an image in which the brightness of the pixel depends on the difference between fat magnetization and water magnetization. An acquisition at t=2a (an echo can not yet be acquired at t=0 since this must first form during t=2a; the fat-water magnetization is anti-parallel at t=3a), thus when fat magnetization and water magnetization are aligned in parallel, yields an image in which the sum of fat magnetization and water magnetization is shown.

The sum and the difference of the two images are now of decisive importance: the sum yields a water image, the difference yields a fat image. It is noted that both images still exhibit an additional, system-dependent phase at the point in time of the measurement. The correction of this phase is necessary but need not be explained in detail within the scope of the discussion herein.

The method described has a significant disadvantage: it does not take into account that both echoes (gradient echo or spin echo) are negatively affected by different decay processes (relaxation processes), namely that the gradient echo is typically affected by the different location-dependent relaxation time of the transversal magnetization that is characterized by $T^*_2$, and the spin echo is typically affected by the plain $T_2$ decay (thus without taking into account the local $B_0$ field inhomogeneities). Actual existing inhomogeneities due to relatively strongly $T^*_2$-dependent or $T_2$-dependent relaxation processes lead to the situation that the components cannot be separated without doubt. In the further proceedings, it is essentially $T^*_2$-sensitive gradient echo techniques that are considered, without limitation of generality.

The solution to this problem is presently avidly researched. All present solution approaches are based on the measurement of additional echoes, typically more than three (up to eleven echoes can be measured). This has the disadvantage of a significant lengthening of the measurement time that is particularly unacceptable for most clinical applications. Moreover, the image resolution is also drastically reduced.

SUMMARY OF THE INVENTION

An object of the present invention is to provide a method and a magnetic resonance tomography apparatus to implement such a method that enable the acquisition of pure fat images and water images dependent on the $T^*_2$ relaxation in a simple manner.

This object is achieved according to the invention by a method for separation of fat images and water images according to the two-point Dixon method dependent on the $T^*_2$ decay that includes the following Steps:

S1: acquire three fat-water images, respectively corresponding to the echo times TE1, TE2, TE3 after the RF excitation pulse, wherein first and third fat-water images exhibit the same phase, S2: calculate a $T^*_2$ map from the two equiphase images, S3: correct the $T^*_2$ influence in one of the two equiphase fat-water images and in the counter-phase fat-water image, S4: reconstruct a pure $T^*_2$-corrected fat image and a pure $T^*_2$-corrected water image according to the two-point Dixon method on the basis of the $T^*_2$-corrected equiphase and counter-phase fat-water images in Step S3.

The magnetization vectors of water (W) and fat (F) are advantageously parallel and point either in the same direction (W+F) or in the opposite direction (W−F). The influence of the aforementioned system-dependent phase is negligible in the further course of the mathematical derivation).

The calculation of the $T^*_2$ map from the two equiphase images ensues according to the invention via the equation $$T^*_2 = \frac{TE3 - TE1}{\ln(S_1) - \ln(S_3)},$$

wherein $$S_i(x, y) = (W(x, y) \pm F(x, y)) \cdot e^{-\frac{TEi}{T^*_2(x,y)}}$$

And represents the measured MR signal for the voxel (x, y) from the i-th echo and i=1, 2, 3.

The correction of the $T^*_2$ influence in one of the two equiphase (i=1, 3) fat water images and in the counter-phase (i=2) fat-water image also ensues according to the invention via the equation $$S'_i = S_i \cdot e^{\frac{TEi}{T^*_2}} = W \pm F$$

Depending on the selected MR imaging sequence, the acquired echoes likewise advantageously represent spin echoes or gradient echo, wherein given spin echoes $T^*_2$ is to be replaced with $T_2$.

Furthermore, the present invention concerns an MR imaging apparatus having a data acquisition unit that acquires three fat-water images respectively corresponding to the echo times TE1, TE2, TE3 after the RF excitation pulse, wherein first and third fat-water image exhibit the same phase, and a processor that calculates a $T^*_2$ map from the two equiphase images and corrects the $T^*_2$ influence in one of the two equiphase fat water images and in the counter-phase fat-water image, an image reconstruction computer that reconstructs a pure $T^*_2$-corrected fat image and a pure $T^*_2$-corrected water image according to the two-point Dixon method on the basis of the corrected equiphase and counter-phase fat-water images corrected in Step S3.

The processor and the image reconstruction computer may be the same device.

The present invention also encompasses a computer-readable medium encoded with programming instructions that cause a processor in which the computer-readable medium is loaded to execute a method in accordance with the invention as described above.

BRIEF DESCRIPTION OF THE DRAWINGS

FIG. 4 shows the measured magnetization of water, fat and the superimposition of both signals.

FIG. 5 shows a gradient echo sequence.

FIG. 6 shows a spin echo sequence.

FIG. 7 shows how three echoes are acquired in succession after an RF excitation pulse, wherein the entire signal curve is modulated with a $T^*_2$-characterized exponential function.

FIG. 8 shows a simplified flow chart of the method according to the invention.

FIG. 9 shows a data flow chart of the method according to the invention.

DESCRIPTION OF THE PREFERRED EMBODIMENTS

Figure 1:
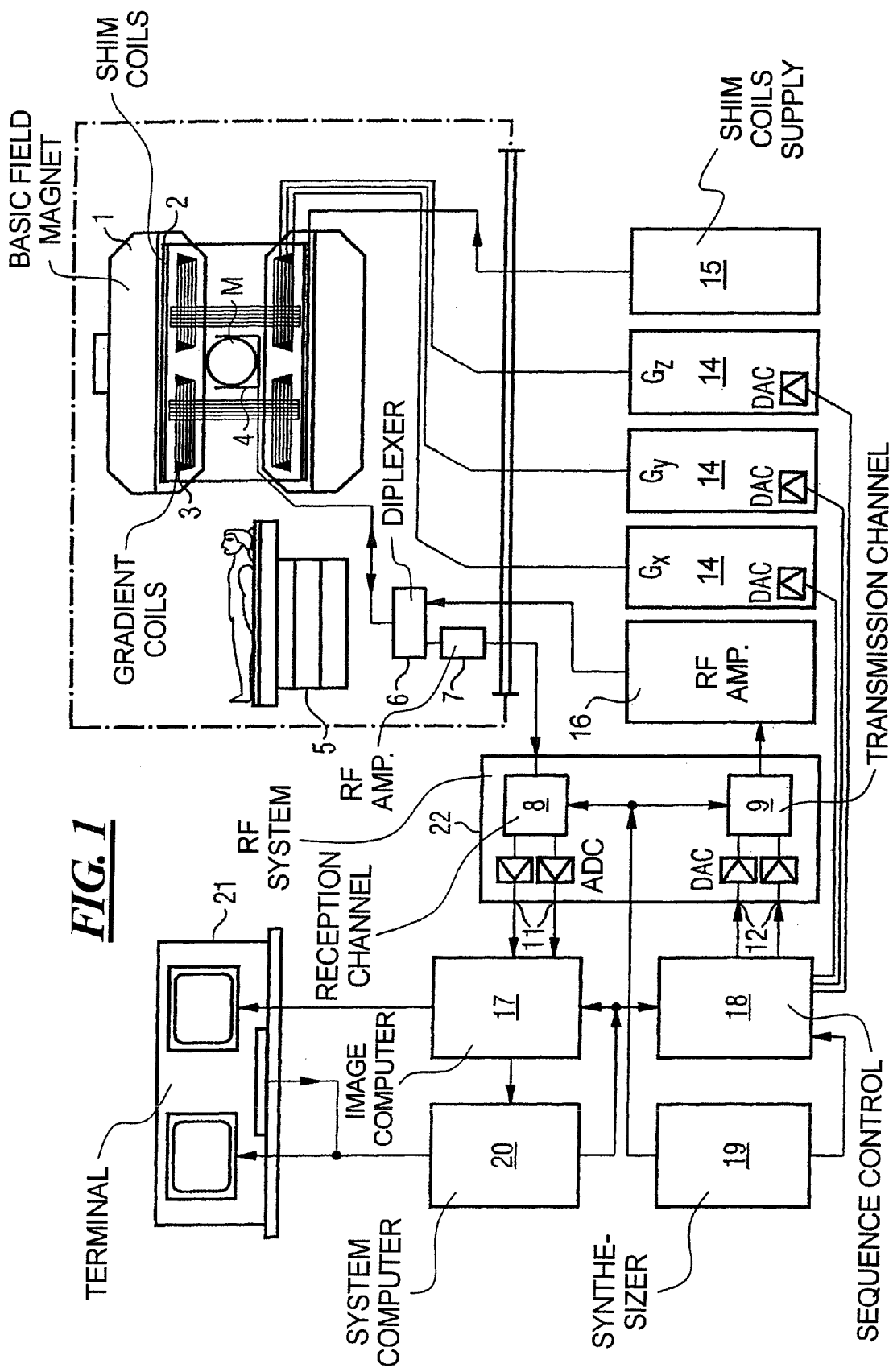
FIG. 1 schematically shows a nuclear magnetic resonance tomography apparatus.

FIG. 1 shows a schematic representation of a magnetic resonance tomography apparatus to generate a nuclear magnetic resonance image of a subject according to the present invention. The basic design of the nuclear magnetic resonance tomography apparatus thereby corresponds to the design of a conventional tomography apparatus, with the differences noted below. A basic field magnet 1 generates a temporally constant, strong magnetic field for polarization or, respectively, alignment of the nuclear spins in the examination region of a subject, for example of a part of a human body to be examined. The high homogeneity of the basic magnetic field that is required for the nuclear spin resonance measurement is defined in a spherical measurement volume M into which the portions of the human body that are to be examined are introduced. Shim plates made of ferromagnetic material are mounted at a suitable point to support the homogeneity requirements and in particular to eliminate temporally invariable influences. Temporally variable influences are eliminated by shim coils 2 that are activated by a shim power supply 15. The shim power supply 15 is connected with the system computer and is controlled thereby.

A cylindrical gradient coil system 3 that consists of three sub-windings is used in the basic field magnet 1. Each sub-winding is supplied by an amplifier 14 with current to generate a linear gradient field in the respective direction of the Cartesian coordinate system. The first sub-winding of the gradient field system 3 generates a gradient $G_x$ in the x-direction, the second sub-winding generates a gradient $G_y$ in the y-direction, and the third sub-winding generates a gradient $G_z$ in the z-direction. Each amplifier 14 has a digital-analog converter that is controlled by a sequence controller 18 for the time-accurate generation of gradient pulses.

Located within the gradient field system 3 are a radio-frequency antenna 4 that converts the radio-frequency pulses emitted by a radio-frequency power amplifier 30 into an alternating magnetic field to excite the nuclei and align the nuclear spins of the subject to be examined or the region of the subject to be examined. The alternating field emanating from the precessing nuclear spins (i.e. normally the nuclear spin echo signals caused by a pulse sequence composed of one or more radio-frequency pulses and one or more gradient pulses) is also converted by the radio-frequency antenna 4 into a voltage that is supplied via an amplifier 7 to a radio-frequency acquisition channel 8 of a radio-frequency system 22. The radio-frequency system 22 furthermore has a transmission channel 9 in which the radio-frequency pulses are generated for the excitation of the nuclear magnetic resonance. The respective radio-frequency pulses are digitally represented in the sequence controller 18 as a series of complex numbers based on a pulse sequence provided by the system computer 20. This number series is supplied as a real part and an imaginary part via respective inputs 12 to a digital-analog converter in the radio-frequency system 22, and from this to a transmission channel 9. In the transmission channel 9, the pulse sequences are modulated on a radio-frequency carrier signal whose base frequency corresponds to the resonance frequency of the nuclear spins in the measurement volume.

The switching from transmission operation to reception operation ensues via a transmission-reception diplexer 6. The radio-frequency antenna 4 radiates the radio-frequency pulses to excite the nuclear spins in the measurement volume M and scans resulting echo signals. The correspondingly acquired nuclear magnetic resonance signals are phase-sensitively demodulated in the acquisition channel 8 of the radio-frequency system 22 and are converted via a respective analog-digital converter into real part and imaginary part of the measurement signal. An image is reconstructed by an image computer 17 from the measurement data so acquired. The administration of the measurement data, the image data and the control programs ensues via the system computer 20. The sequence controller 18 monitors the generation of the respective desired pulse sequences and the corresponding scanning of k-space based on a specification with control programs. In particular, the sequence controller 18 controls the time-accurate switching of the gradients, the emission of the radio-frequency pulses with defined phase and amplitude and the acquisition of the nuclear magnetic resonance signals. The time base for the radio-frequency system 22 and the sequence controller 18 is provided by a synthesizer 19. The selection of corresponding control programs to generate a nuclear magnetic resonance image as well as the presentation of the generated nuclear magnetic resonance image ensues via a terminal 21 that comprises a keyboard and one or more monitors (screens).

Figure 2:
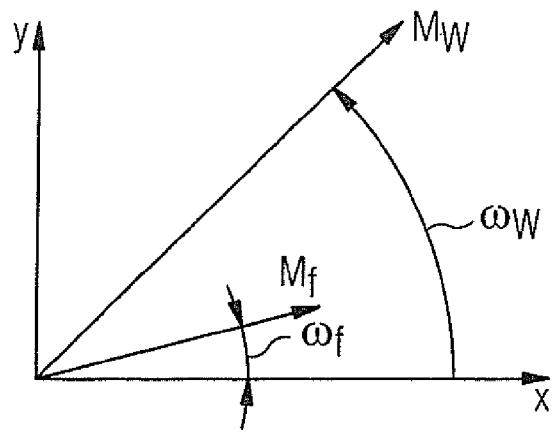
FIG. 2 depicts the transverse magnetization component of fat and water after a 90° pulse in a laboratory system.

FIG. 2 shows the transverse magnetization components of fat and water after a 90° pulse in a laboratory system. The volume element contains both the water signal and the fat signal. Mw is the magnetization of water; Mf is the magnetization of the fat. vw and vf are the Larmor frequencies of the water protons and fat protons ($\omega=2\pi v$).

Figure 3:
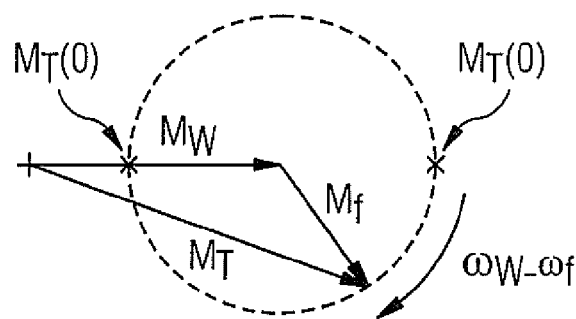
FIG. 3 shows the situation in a rotating reference system.
Figure 3:
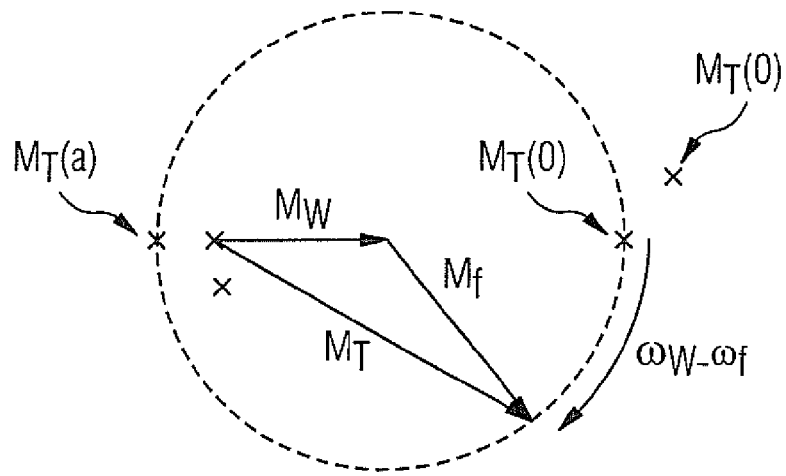

FIG. 3 shows the signal in the rotating reference system: the total magnetization of water is greater than that of fat (|Mw|>|Mf|) in the upper drawing. In the lower drawing, the total magnetization of fat is greater than that of water (|Mf|>|Mw|).

The variation of the total magnetization MT shown in FIG. 3 leads to a periodic change of the measured total nuclear magnetic resonance signal.

FIG. 4 shows the measured magnetization of water, fat and the total nuclear magnetic resonance signal via superimposition of the two signals.

According to the present invention, the magnetic resonance tomography apparatus is operated with a gradient echo sequence or with a spin echo sequence. FIGS. 3 and 4 serve as a short explanation and represent general echo sequences that must be correspondingly modified in a two- or multi-point Dixon technique.

As shown in FIG. 5, a rephasing with regard to a slice-selection gradient $G_S$ and a pre-dephasing with regard to a readout gradient $G_R$ occur in the gradient echo sequence. Through this gradient switching, the dephasing of the transversal magnetization that is caused by the gradient is compensated so that an echo signal arises that is designated as a gradient echo. The basic idea is thus that the transversal magnetization is restored after the signal readout and can be used for the next sequence pass. The echo signal in the gradient echo sequence is generated via gradient reversal of the frequency coding gradients.

The spin echo sequence is shown in FIG. 6. In the spin echo sequence, a dephasing frequency coding or, respectively, readout gradient switching (Gr) follows the 90° excitation pulse. After deactivating the gradient (Gr), a phase shift remains. A subsequent 180° radio-frequency pulse produces an inversion of the phase shift. If the gradient (Gr) is activated again in the same manner as before, it acts in a rephasing manner. The phase shift is thus again reduced in terms of magnitude. The refocusing of the nuclear spins for spin echo is implemented at the point in time of the complete rephasing.

In both techniques, the repetition time $T_R$ is the time after which one RF excitation pulse follows the other. After the time $T_E$, the echo signal occurs and can be acquired by means of readout gradient $G_R$.

In the phase coding, a gradient field whose strength is decreased (↓) or, respectively, increased (↑) step-by-step by the amount $\Delta G_P$ in each sequence pass is activated for a fixed time period before the acquisition of the signal.

It should be noted that the system frequency is normally tuned to water so that the water spins would not precess in the rotating reference system, i.e. would be "on-resonant" (assuming that the basic field B0 would be absolutely homogeneous). The precession angle $\beta_w$ if water would be zero ($\beta_w=0$). The other spin collective (fat) would thus precess in the rotating reference system of water so that it would be aligned at the angle $\beta_F=180°$ (thus antiparallel to the spin collective of the water) after a time $\Delta T_E$ and would be aligned at $\beta_F=360°$ (i.e. parallel to the spin collective of the water) after the time $2\Delta T_E$.

The $T^*_2$ relaxation is also actually not of equal magnitude at every point of the fat-water images to be imaged (W–F or, respectively, W+F). For this reason, according to the invention a $T^*_2$ map is generated for every fat-water image of the same phase (thus either from two W–F images or from two W+F images). Both the W–F image and the W+F image can then be $T^*_2$-corrected with this $T^*_2$ map, whereby respectively, cleanly separated $T^*_2$-corrected fat images and water images can be generated on the basis of these images after the two-point Dixon reconstruction.

In the following it is shown how a $T^*_2$ map (and therefore ultimately a $T^*_2$-corrected W+F image and a likewise $T^*_2$-corrected W–F image) can be calculated mathematically from the acquired fat-water images (either from two W–F images and one W+F image or from two W+F images and one W–F image).

After the α RF excitation pulse (for example α=90°), Echo1 (MR signal 1) is acquired after the time TE1, Echo2 (MR signal 2) is acquired after the time TE2 and Echo 3 (MR signal 3) is acquired after the time TE3. The signal curve of the three echoes is modulated with a $T^*_2$-dependent exponential function (see FIG. 7):

$$e^{-\frac{t}{T^*_2}}$$

After the image reconstruction, the MR signal $$S_1(x,y) = (W(x,y) \pm F(x,y)) \cdot e^{-\frac{TE1}{T^*_2(x,y)}} \quad (1)$$

$$S_2(x,y) = (W(x,y) \pm F(x,y)) \cdot e^{-\frac{TE2}{T^*_2(x,y)}} \quad (2)$$

$$S_3(x,y) = (W(x,y) \pm F(x,y)) \cdot e^{-\frac{TE3}{T^*_2(x,y)}} \quad (3)$$

is acquired for each pixel (x, y) (for each voxel (x, y, z) in a 3D volume) at the times TE1, TE2 and TE3 after each RF pulse of the applied MRT sequence. $S_i(x, y)$ is thereby the measured MR signal for the voxel (x, y) or, respectively, (x, y, z) from the i-th echo. W(x, y) represents the water signal, F(x, y) the fat signal. Without limitation of the generality, as is seen fat and water are in phase (W+F) in the first and third echo but counter-phase (W−F) in the second echo. The system-dependent phase is also negligible again here.

A relationship to the pixel-based calculation of the desired $T^*_2$ map can now be obtained from Equations (1) and (3). Although $S_i$, W, F and $T^*_2$ are always functions of the coordinates (x, y) or, respectively, (x, y, z), the latter are omitted for the sake of better clarity. The following Equations (4) and (5) are obtained by taking the logarithm of Equations (1) and (3) ($\ln(S_i)$ is the natural log)

$$\ln(S_1) = \ln(W + F) + \left(-\frac{TE1}{T_2^*}\right) \quad (4)$$

$$\ln(S_3) = \ln(W + F) + \left(-\frac{TE3}{T_2^*}\right) \quad (5)$$

Equation (6)

$$T_2^* = \frac{TE3 - TE1}{\ln(S_1) - \ln(S_3)} \quad (6)$$

with which a current $T^*_2$ map based on the measurements $S_1$ and $S_3$ can be generated pixel for pixel is obtained by subtraction of Equation (5) from Equation (4).

With the $T^*_2$ map, the $S_1$ measurements and $S_2$ measurements can in turn be $T^*_2$-corrected, whereby $T^*_2$-corrected fat-water images $T^*_2$ and $T^*_2$ are obtained that ultimately allow a two-point Dixon reconstruction of pure $T^*_2$-corrected fat images and water images:

$$S_1' = S_1 \cdot e^{\frac{TE1}{T_2^*}} = W + F \quad (7)$$

$$S_2' = S_2 \cdot e^{\frac{TE2}{T_2^*}} = W - F \quad (8)$$

The subtraction of Equation (8) from Equation (7) leads to a pure $T^*_2$-corrected fat image (2F); the addition of Equation (8) with Equation (7) leads (after correction of the system-dependent phase) to a pure $T^*_2$-corrected water image (2W).

A simplified flow diagram of the method according to the invention is shown in FIG. 8. A spin echo measurement or a gradient echo measurement with the acquisition of three respective echoes ensues in Step S1, wherein three different fat-water images are generated. The first image and third image thereby exhibit a common phase. In Step S2 a $T^*_2$ map is calculated from the two equiphase images of the three fat-water images. The $T^*_2$-influence in two counter-phase fat-water images is corrected in Step S3. Finally, an image reconstruction according to the two-point Dixon method is implemented in Step S4 on the basis of the $T^*_2$-corrected fat-water images.

For further illustration, a data flow diagram of the method according to the invention is shown in FIG. 9:

In Line 1 it is shown how three echoes are acquired in succession after an RF excitation pulse. In this case a counter-phase fat-water image (W−F) is first, then an equiphase image (W+F) and finally a counter-phase image (W−F) again. An equiphase fat-water image (W+F) can just as well be first, then a counter-phase (W−F) image and finally an equiphase image (W+F) again. The three original images that can be generated from the three echoes after the completion of the entire image sequence are depicted in Line 2. Line 3 shows the $T^*_2$ map that is calculated from the two counter-phase fat-water images (W−F). Line 4 shows how, with the $T^*_2$ map, a respective counter-phase fat-water image and equiphase fat-water image that this time are $T^*_2$-corrected are formed from a counter-phase fat-water image and an equiphase fat-water image. Finally, in Line 5 it is shown how a pure fat image (2F) and a pure water image (2W) are reconstructed from the two $T^*_2$-corrected fat-water images via the two-point Dixon method.

The method according to the invention does not represent an exact solution to the $T^*_2$ correction. In reality, a pixel or voxel consists of different water and fat portions that respectively also exhibit different $T^*_2$-relaxation times. The $T^*_2$-calculation from only two measurement points is additionally not exact. Nevertheless, the method according to the invention increases the clinical diagnostic value of reconstructed, separated fat-water images since it contributes to the ability to differentiate at the boundary of fat-water regions, in particular contributes to facilitating (and therefore improving) this via a different $T^*_2$ influence.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for separation of fat images and water images according to the two-point Dixon method dependent on the $T^*_2$ decay, comprising the steps of:
   (S1): with a magnetic resonance data acquisition unit, acquiring three fat-water images from a patient in the unit, respectively corresponding to echoes at echo times TE1, TE2, TE3 after an RF excitation pulse, wherein a first and a third of said fat-water images exhibit the same phase;
   (S2): in a processor, calculating a $T^*_2$ map from the two equiphase images;
   (S3): in said processor, correcting the $T^*_2$ influence in one of the two equiphase fat-water images and in the counter-phase fat-water image; and
   (S4): in an image computer, reconstructing a pure $T^*_2$-corrected fat image and a pure $T^*_2$-corrected water image according to the two-point Dixon method using the $T^*_2$-corrected equiphase and counter-phase fat-water images from Step (S3).

2. A method according to claim 1, comprising acquiring said fat-water images in step (S1) with the magnetization vectors of water (W) and fat (F) being parallel and pointing either in the same direction (W+F) or in the opposite direction (W−F).

3. A method according to claim 2, wherein step (S2) comprises:
   calculating the $T^*_2$ map from the two equiphase images ensues by the equation $$T_2^* = \frac{TE3 - TE1}{\ln(S_1) - \ln(S_3)},$$

wherein $$S_i(x, y) = (W(x, y) \pm F(x, y)) \cdot e^{-\frac{TEi}{T_2^*(x,y)}}$$

And represents the measured MR signal for the voxel (x, y) from the i-th echo and i=1, 2, 3.

4. A method according to claim 3, wherein Step (S3) comprises:

correcting the $T^*_2$ influence in one of the two equiphase (i=1, 3) fat water images and in the counter-phase (i=2) fat-water image ensues by the equation $$S'_i = S_i \cdot e^{\frac{TE1}{T^*_2}} = W \pm F.$$

5. A method according to claim 1, comprising, in step (S1):

acquiring said echoes as spin echoes or gradient echoes, and for spin echoes, replacing $T^*_2$ with $T_2$.

6. A magnetic resonance apparatus for separation of fat images and water images according to the two-point Dixon method dependent on the $T^*_2$ decay, comprising:

a magnetic resonance data acquisition unit;

a control unit that operates said magnetic resonance data acquisition unit to acquire three fat-water images from a patient in the unit, respectively corresponding to echoes at echo times TE1, TE2, TE3 after an RF excitation pulse, wherein a first and a third of said fat-water images exhibit the same phase;

a processor configured to calculate a $T^*_2$ map from the two equiphase images;

said processor being configured to correct the $T^*_2$ influence in one of the two equiphase fat-water images and in the counter-phase fat-water image; and an image computer configured to reconstruct a pure $T^*_2$-corrected fat image and a pure $T^*_2$-corrected water image according to the two-point Dixon method using the $T^*_2$-corrected equiphase and counter-phase fat-water images.

7. A non-transitory computer-readable medium loadable into a computerized system that operates a magnetic resonance imaging apparatus, said non-transitory computer-readable medium being encoded with programming instructions, and said programming instructions causing said computerized system to:

(operate a magnetic resonance data acquisition unit of the magnetic resonance imaging apparatus to acquire three fat-water images from a patient in the unit, respectively corresponding to echoes at echo times TE1, TE2, TE3 after an RF excitation pulse, wherein a first and a third of said fat-water images exhibit the same phase;

Calculate a $T^*_2$ map from the two equiphase images;

correct the $T^*_2$ influence in one of the two equiphase fat-water images and in the counter-phase fat-water image; and reconstruct a pure $T^*_2$-corrected fat image and a pure $T^*_2$-corrected water image according to the two-point Dixon method using the $T^*_2$-corrected equiphase and counter-phase fat-water images.

* * * * *